(12) United States Patent
Kantor et al.

(10) Patent No.: US 11,306,104 B2
(45) Date of Patent: Apr. 19, 2022

(54) SOLID STATE FORMS OF RELUGOLIX

(71) Applicant: TEVA PHARMACEUTICALS INTERNATIONAL GMBH, Jona (CH)

(72) Inventors: Hana Kantor, Ostrava (CZ); Roman Gabriel, Olomouc (CZ); Pavel Kolesa, Haj Ve Slezsku (CZ); Alexandr Jegorov, Dobra Voda (CZ)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 16/980,507

(22) PCT Filed: Mar. 14, 2019

(86) PCT No.: PCT/US2019/022169
§ 371 (c)(1),
(2) Date: Sep. 14, 2020

(87) PCT Pub. No.: WO2019/178304
PCT Pub. Date: Sep. 19, 2019

(65) Prior Publication Data
US 2021/0017188 A1  Jan. 21, 2021

Related U.S. Application Data

(60) Provisional application No. 62/661,752, filed on Apr. 24, 2018, provisional application No. 62/642,649, filed on Mar. 14, 2018.

(51) Int. Cl.
*C07D 495/04* (2006.01)
*A61K 9/00* (2006.01)

(52) U.S. Cl.
CPC .......... *C07D 495/04* (2013.01); *A61K 9/0053* (2013.01); *C07B 2200/13* (2013.01)

(58) Field of Classification Search
None
See application file for complete search history.

(56) References Cited

FOREIGN PATENT DOCUMENTS

| EP | 1591446 A1 | 11/2005 |
|----|------------|---------|
| WO | 2014051164 A2 | 4/2014 |
| WO | 2019020102 A1 | 1/2019 |

OTHER PUBLICATIONS

Kazuhiro Miwa, et al. "Discovery of I-{4-[1-(2,6-Difluorobenzyl)-5-[(dimethyla mino)methyl]-3-(6-methoxypyridazin-3-yl)-2,4-dioxo-I,2,3,4-tetrahydrothieno[2,3- d ]pyrimidin-6-yl]phenyl}-3-methoxyurea (TAK-385) as a Potent, Orally Active, Non-Peptide Antagonist of the Human Gonadotropin-Releasing Hormone Receptor", Journal of Medicinal Chemistry, vol. 54, pp. 4998-5012 (2011).

International Search Report and Written Opinion issued in corresponding International Appl. No: PCT/US2019/022169 dated May 16, 2019 (36 pages).

*Primary Examiner* — Brian J Davis
(74) *Attorney, Agent, or Firm* — Carter, DeLuca & Farrell LLP

(57) ABSTRACT

The present disclosure provides solid state forms of Relugolix, crystalline forms of Relugolix, pharmaceutical compositions thereof, and pharmaceutical formulations thereof. Methods for producing these forms of Relugolix, pharmaceutical compositions, and pharmaceutical formulations are also provided.

12 Claims, 9 Drawing Sheets

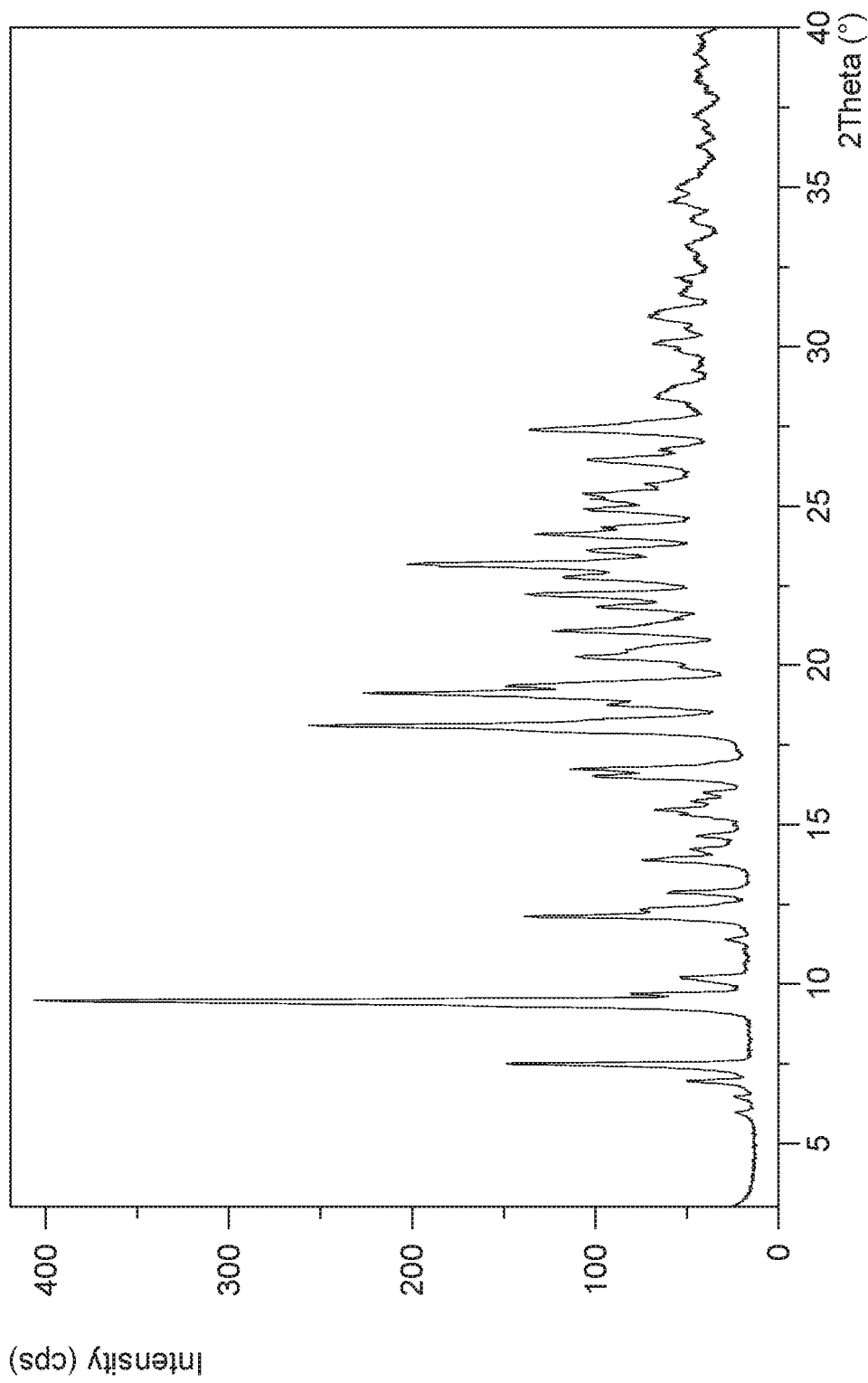
Figure 1: A XRPD pattern of Relugolix Form F

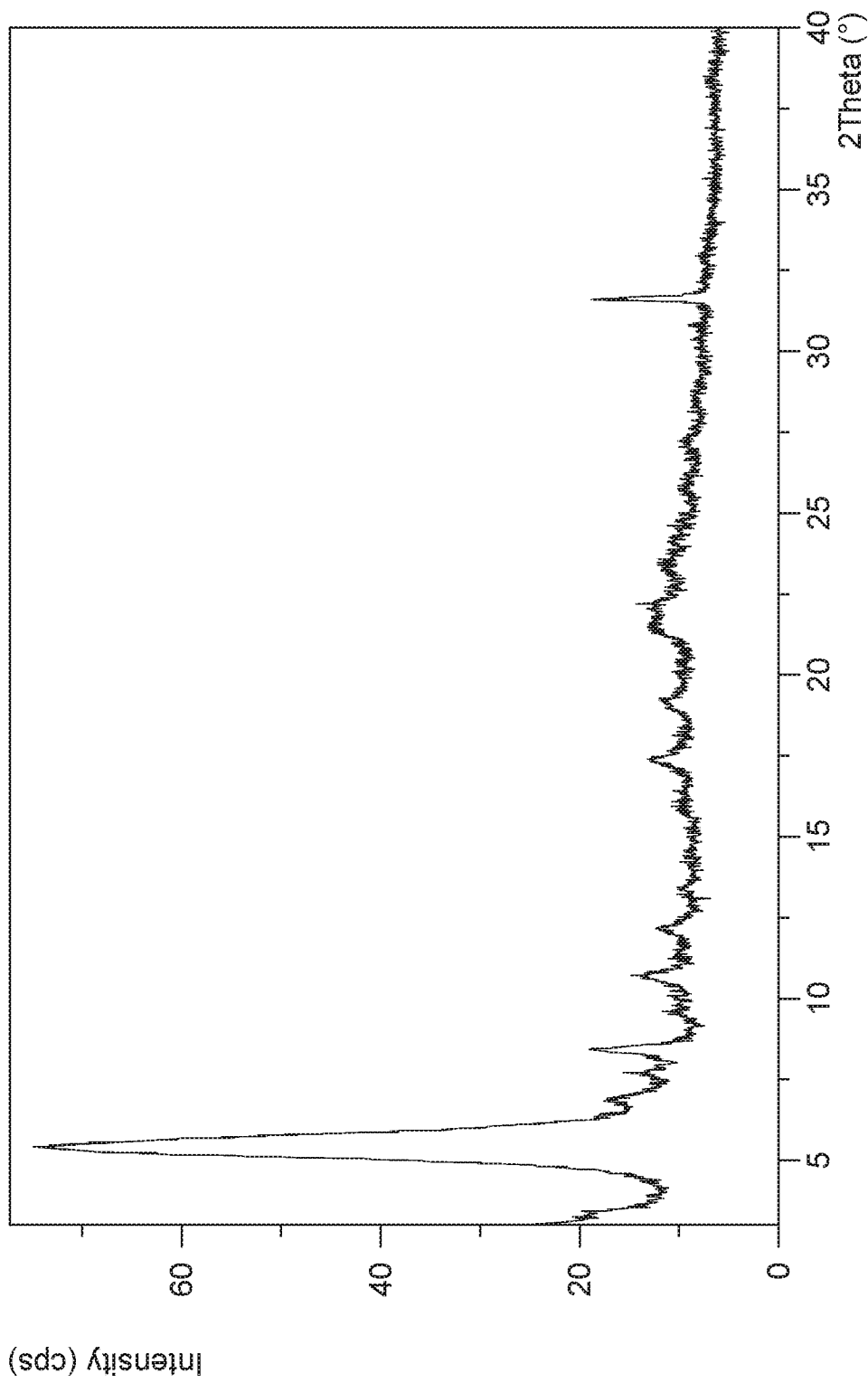
Figure 2: A XRPD pattern of Relugolix Form G

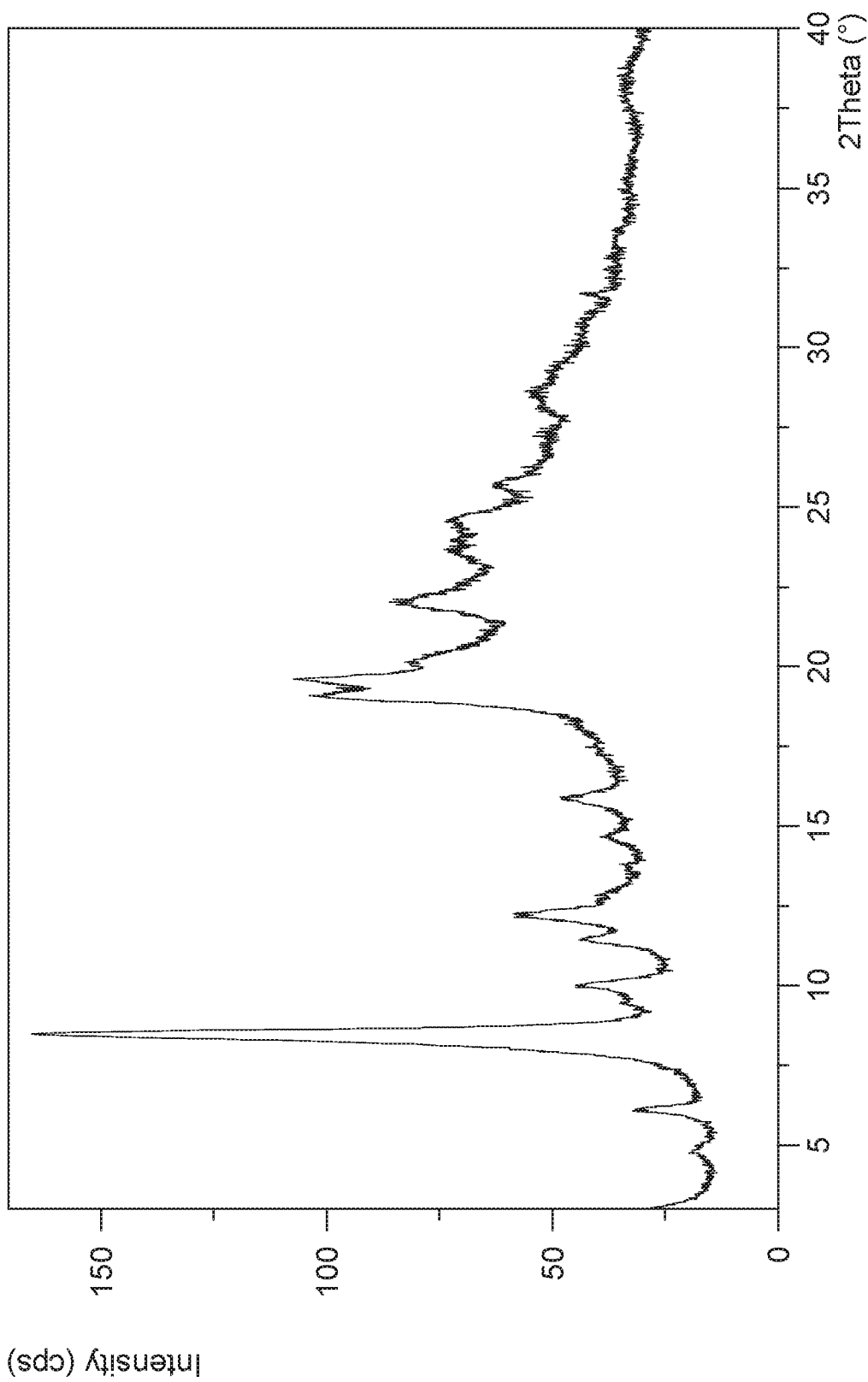
Figure 3: A XRPD pattern of Relugolix Form H

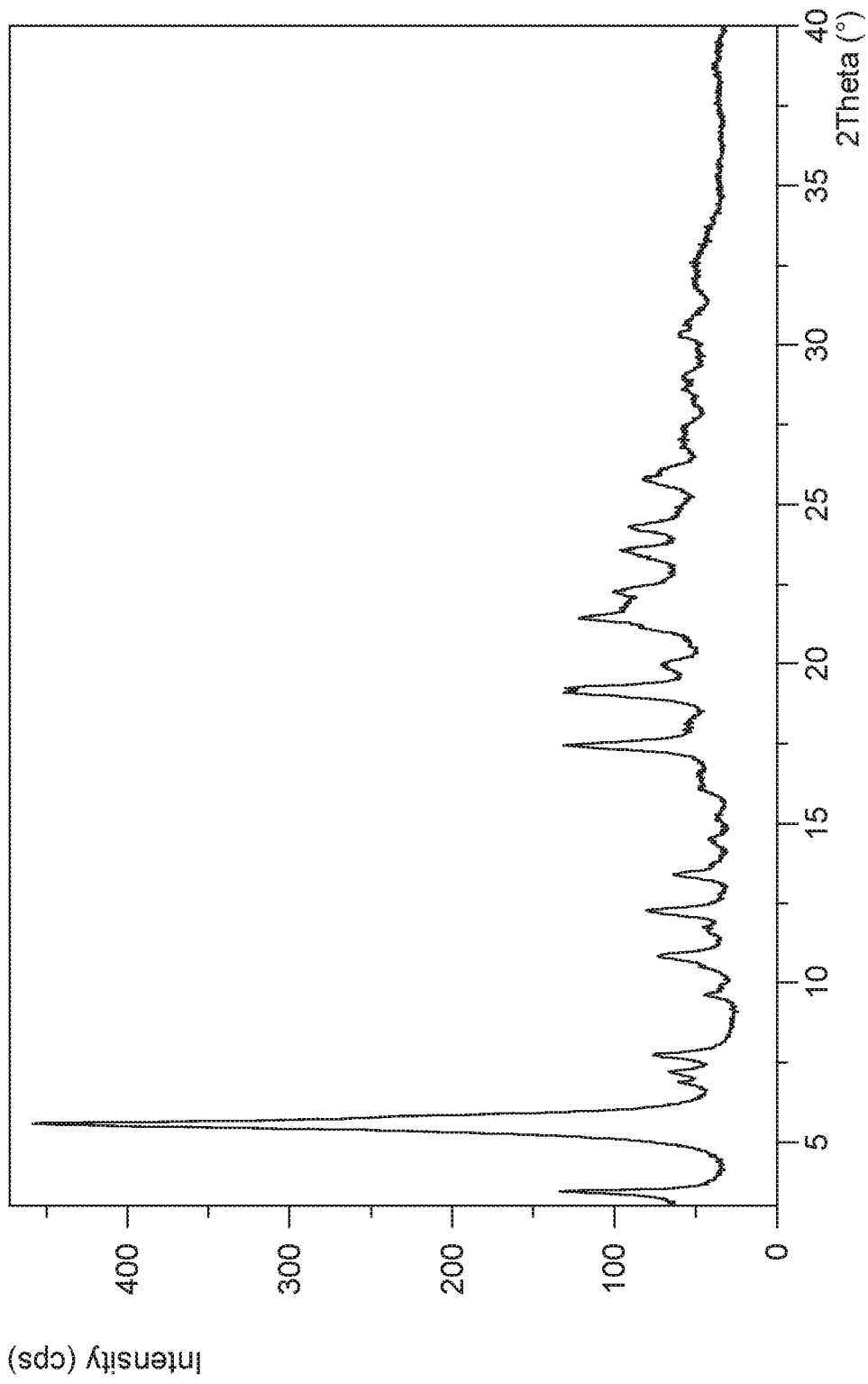
Figure 4: A characteristic X-ray powder diffraction pattern (XRPD) of polymorphically pure Relugolix Form G

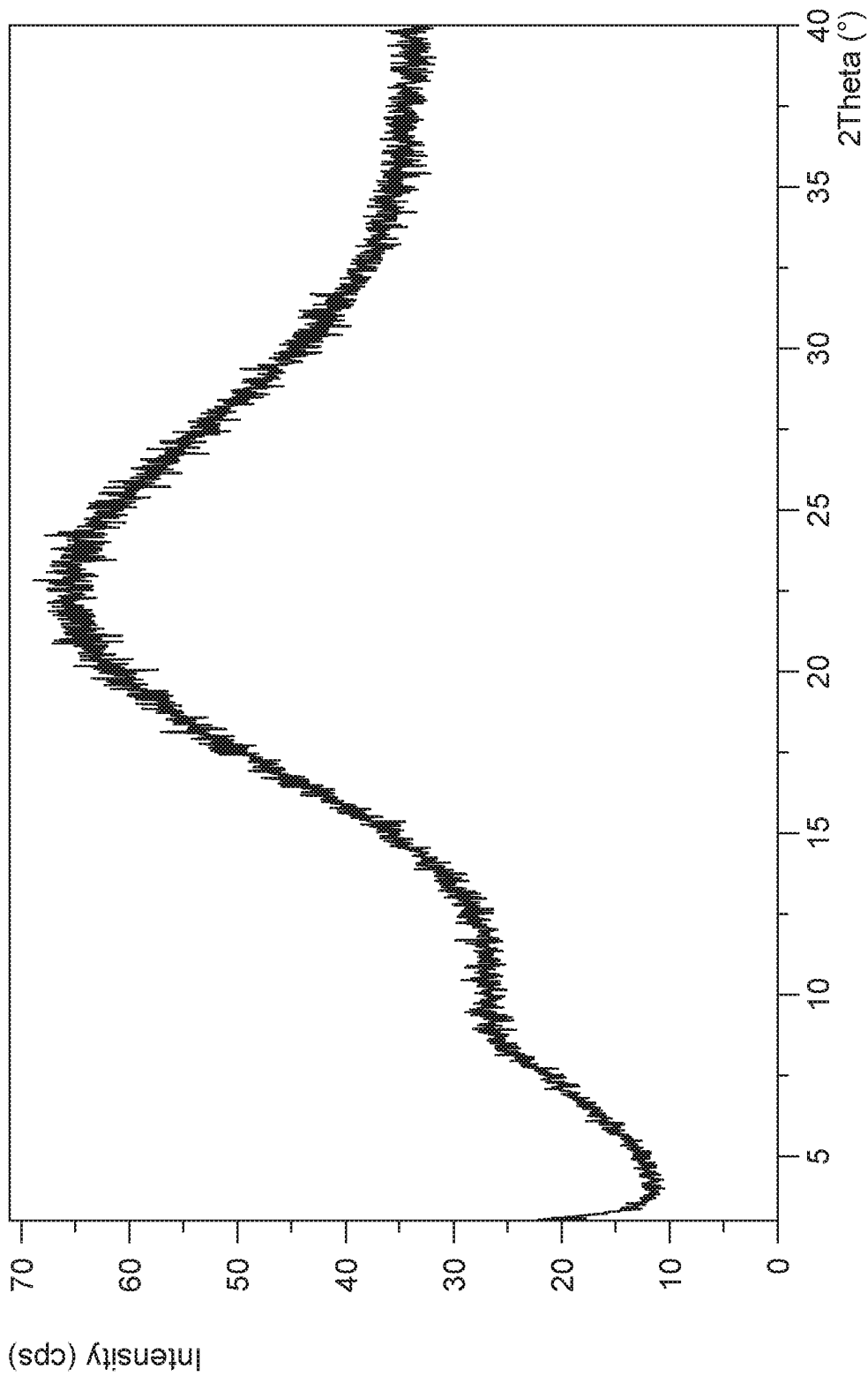
Figure 5: A characteristic X-ray powder diffraction pattern (XRPD) of amorphous Relugolix

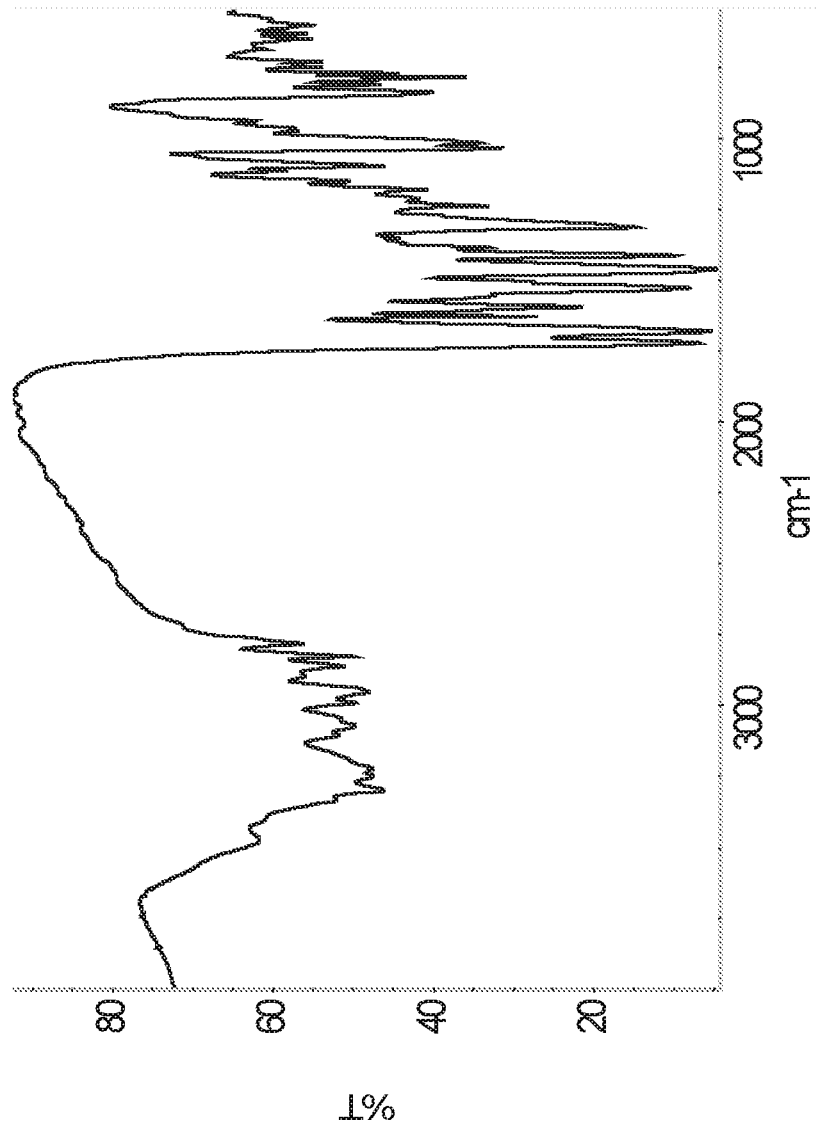

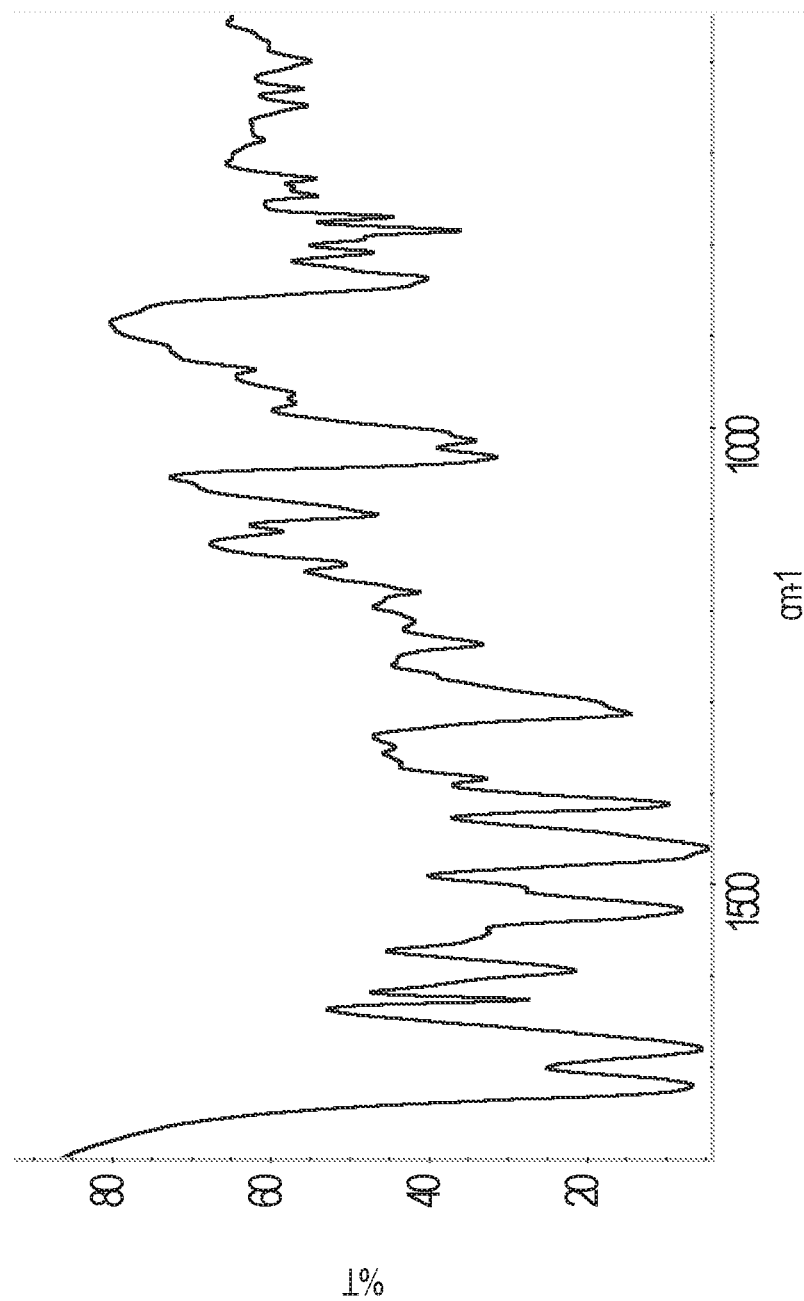
Figure 6b: A FT-IR spectrum of Relugolix Form F (zoomed-in)

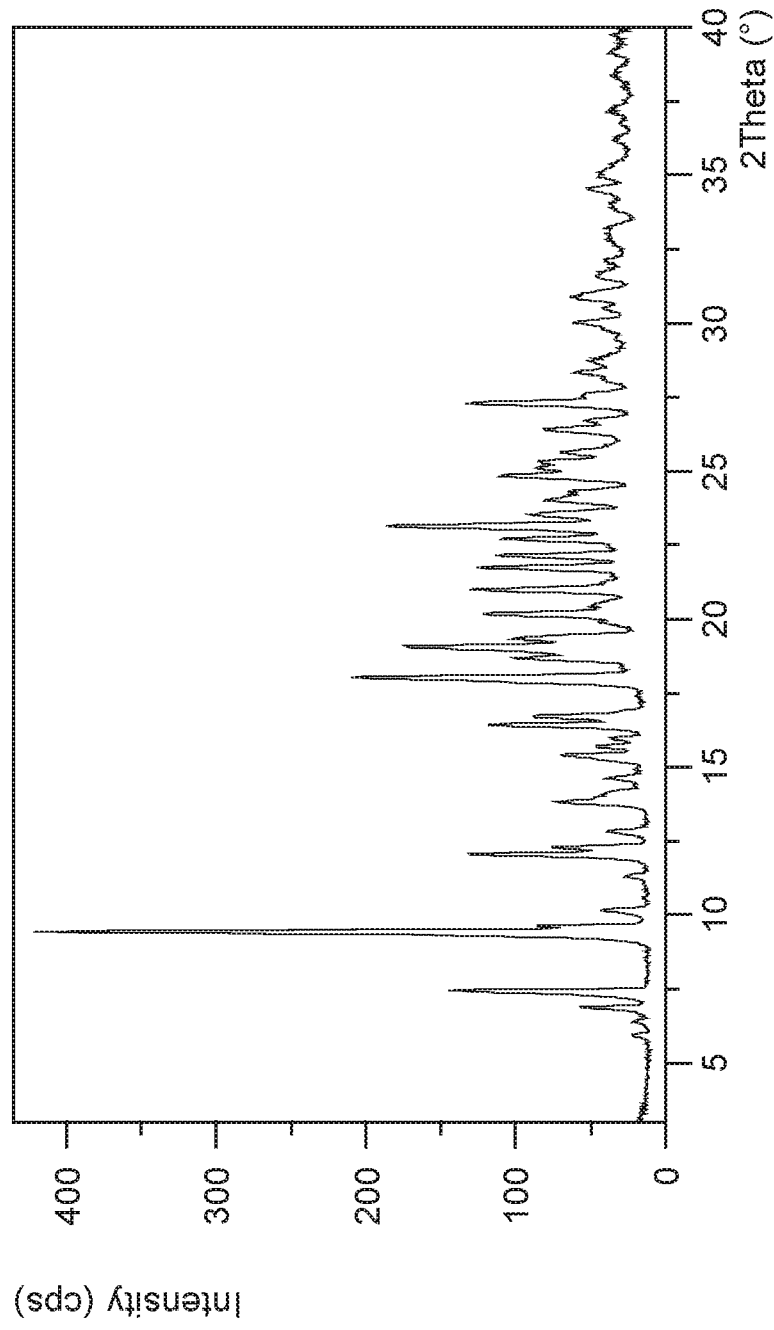
Figure 7: XRPD pattern of Relugolix Form F (anhydrous)

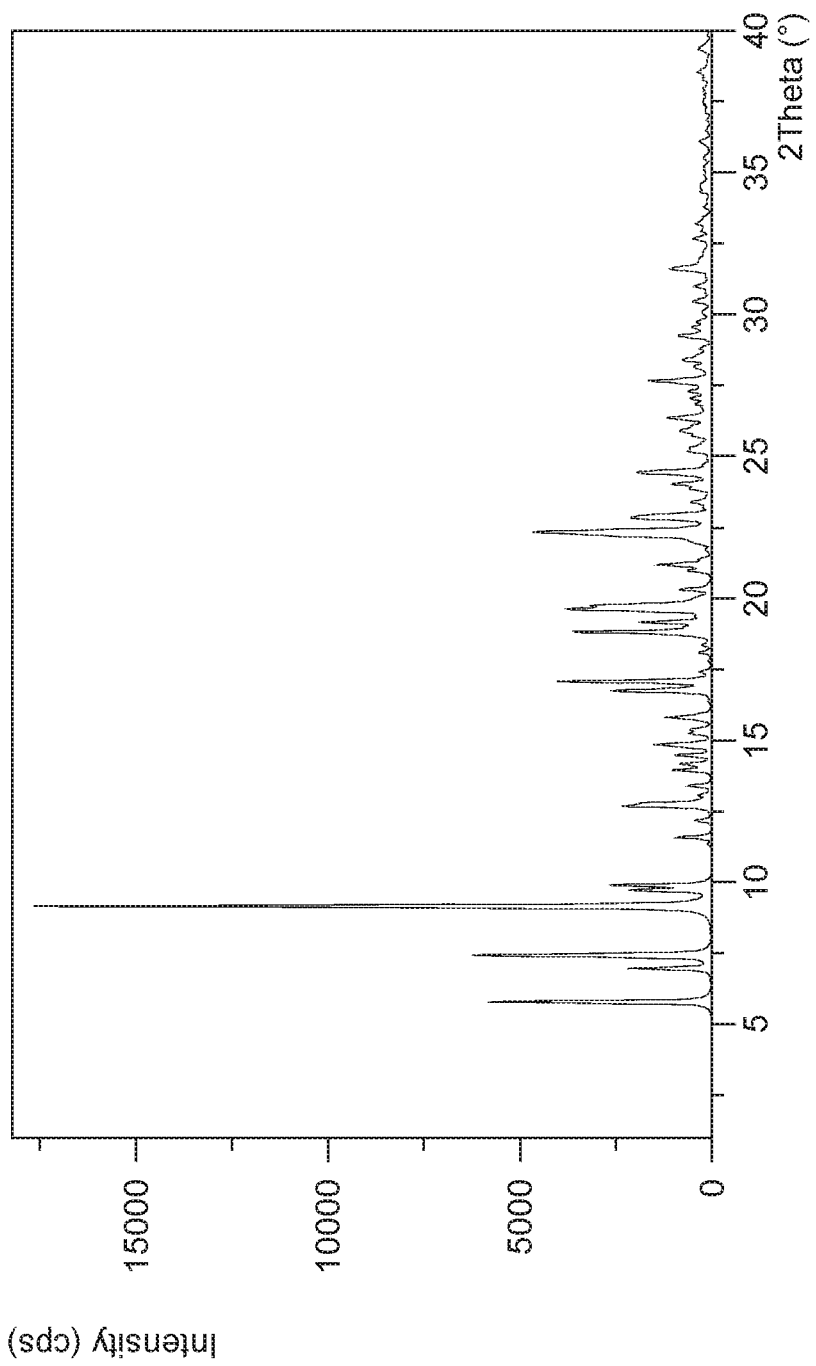

SOLID STATE FORMS OF RELUGOLIX

CROSS REFERENCE TO RELATED APPLICATIONS

This application is a National Stage of, and claims priority to and the benefit of, International Patent Application No. PCT/US2019/022169 filed Mar. 14, 2019, which, in turn, claims the benefit of, and priority to, U.S. Provisional Patent Application No. 62/642,649, filed Mar. 14, 2018 and U.S. Provisional Patent Application No. 62/661,752, filed Apr. 24, 2018, the entire disclosures of each of which are incorporated by reference herein.

FIELD OF THE DISCLOSURE

The present disclosure encompasses solid state forms of Relugolix, in embodiments crystalline polymorphs of Relugolix, processes for preparation thereof, and pharmaceutical compositions thereof.

BACKGROUND OF THE DISCLOSURE

Relugolix's chemical name is 1-(4-(1-(2,6-difluorobenzyl)-5-((dimethylamino)methyl)-3-(6-methoxypyridazin-3-yl)-2,4-dioxo-1,2,3,4-tetrahydrothieno(2,3-d)pyrimidin-6-yl)phenyl)-3-methoxyurea, having the following chemical structure:

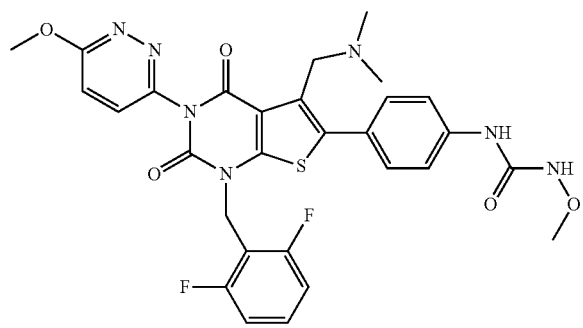 [SMILES: CONC(=O)Nc1ccc(-c2sc3c(c2CN(C)C)c(=O)n(-c2ccc(OC)nn2)c(=O)n3Cc2c(F)cccc2F)cc1]

Relugolix is a selective antagonist of Gonadotropin-Releasing Hormone Receptor, under development for the treatment of certain pathologies, e.g., endometriosis, uterine leiomyoma, and prostate cancer.

The compound is described in PCT publication WO 2004/067535. PCT publication WO 2010/026993 relates to pharmaceutical compositions containing, inter alia, Relugolix. WO 2014/051164 relates to processes and crystalline forms of Relugolix. WO 2016/136849 relates to a solid preparation, e.g., tablet, containing Relugolix. In addition, J. Med. Chem., 2011, 54 (14), pp. 4998-5012, refers, inter alia, to pharmacological and chemical aspects of this molecule.

Polymorphism, the occurrence of different crystalline forms, is a property of some molecules and molecular complexes. A single molecule may give rise to a variety of polymorphs having distinct crystal structures and physical properties, like melting point, thermal behaviors (e.g., measured by thermogravimetric analysis—"TGA", or differential scanning calorimetry—"DSC"), X-ray diffraction (XRD) pattern, infrared absorption fingerprint, and solid state ($^{13}$C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example, by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Relugolix.

SUMMARY OF THE DISCLOSURE

The present disclosure provides crystalline polymorphs of Relugolix, processes for preparation thereof, and pharmaceutical compositions thereof. These crystalline polymorphs can be used to prepare other solid state forms of Relugolix, Relugolix salts and their solid state forms.

The present disclosure provides crystalline polymorphs of Relugolix for use in the preparation of pharmaceutical compositions and/or formulations for use in medicine, in embodiments for the treatment of endometriosis, uterine leiomyoma, and/or prostate cancer.

The present disclosure also encompasses the use of crystalline polymorphs of Relugolix of the present disclosure for the preparation of pharmaceutical compositions and/or formulations.

In another aspect, the present disclosure provides pharmaceutical compositions including crystalline polymorphs of Relugolix according to the present disclosure.

In yet another embodiment, the present disclosure encompasses pharmaceutical formulations including the described crystalline polymorphs of Relugolix, or pharmaceutical compositions including the described crystalline polymorphs of Relugolix and at least one pharmaceutically acceptable excipient.

The present disclosure includes processes for preparing the above mentioned pharmaceutical compositions. The processes include combining a crystalline polymorph of Relugolix with at least one pharmaceutically acceptable excipient.

The crystalline polymorph of Relugolix as defined herein and the pharmaceutical compositions or formulations of the crystalline polymorph of Relugolix may be used as medicaments, in embodiments for the treatment of endometriosis, uterine leiomyoma, and/or prostate cancer.

The present disclosure also provides methods of treating endometriosis, uterine leiomyoma, and/or prostate cancer, by administering a therapeutically effective amount of a crystalline polymorph of Relugolix of the present disclosure, or at least one of the above pharmaceutical compositions or formulations, to a subject suffering from endometriosis, uterine leiomyoma, prostate cancer, or otherwise in need of the treatment.

The present disclosure also provides the uses of crystalline polymorphs of Relugolix of the present disclosure, or at least one of the above pharmaceutical compositions or formulations, for the manufacture of medicaments for treating e.g., endometriosis, uterine leiomyoma and/or prostate cancer.

BRIEF DESCRIPTION OF THE DRAWINGS

FIG. 1 shows a characteristic X-ray powder diffraction pattern (XRPD) of Relugolix Form F (as hemihydrate).

FIG. 2 shows a characteristic X-ray powder diffraction pattern (XRPD) of Relugolix Form G.

FIG. 3 shows a characteristic X-ray powder diffraction pattern (XRPD) of Relugolix Form H.

FIG. 4 shows a characteristic X-ray powder diffraction pattern (XRPD) of polymorphically pure Relugolix Form G.

FIG. 5 shows a characteristic X-ray powder diffraction pattern (XRPD) of amorphous Relugolix.

FIG. 6a shows a characteristic FT-IR spectrum of Relugolix Form F (full range).

FIG. 6b shows a characteristic FT-IR spectrum of Relugolix Form F (zoomed-in).

FIG. 7 shows a characteristic X-ray powder diffraction pattern (XRPD) of Relugolix Form F (anhydrous).

FIG. 8 shows a calculated XRPD pattern of Relugolix Form J (determined from crystal data obtained at 180 K).

DETAILED DESCRIPTION OF THE DISCLOSURE

The present disclosure encompasses solid state forms of Relugolix, such as crystalline polymorphs of Relugolix, processes for preparation thereof, and pharmaceutical compositions thereof.

Solid state properties of Relugolix and crystalline polymorphs thereof can be influenced by controlling the conditions under which Relugolix and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Relugolix described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Relugolix. In some embodiments of the disclosure, the described crystalline polymorph of Relugolix may contain from about 1% to about 20% (w/w), from about 5% to about 20% (w/w), or from about 5% to about 10% (w/w) of one or more other crystalline polymorph of the same Relugolix.

Depending on any other crystalline polymorphs with which a comparison is made, the crystalline polymorphs of Relugolix of the present disclosure have advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Relugolix referred to herein as being characterized by graphical data "as depicted in" or "as substantially depicted in" a Figure will thus be understood to include any crystal forms of Relugolix characterized with the graphical data having such small variations, as are well known to the skilled person, in comparison with the Figure.

As used herein, and unless stated otherwise, the term "anhydrous" in relation to crystalline forms of Relugolix, relates to a crystalline form of Relugolix which does not include any crystalline water (or other solvents) in a defined, stoichiometric amount within the crystal. Moreover, an "anhydrous" form would typically not contain more than 1% (w/w), of either water or organic solvents as measured, for example, by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless indicated otherwise, the term "wet crystalline form" refers to a polymorph that was not dried using any conventional techniques to remove residual solvent. Examples of such conventional techniques can be, but are not limited to, evaporation, vacuum drying, oven drying, drying under nitrogen flow, etc.

As used herein, and unless indicated otherwise, the term "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

As used herein, the term "isolated" in reference to a crystalline polymorph of Relugolix of the present disclosure corresponds to a crystalline polymorph of Relugolix that is physically separated from the reaction mixture in which it is formed.

As used herein, unless stated otherwise, the XRPD measurements are taken using copper Kα radiation wavelength 1.54187 Å (1.5419 Å). XRPD peaks reported herein are measured using CuK α radiation, λ=1.54187 Å (1.5419 Å), typically at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in embodiments about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

As used herein, the term "crystalline '816" refers to the crystalline form described in US 2018/0319816 (counterpart of WO 2014/051164), FIG. 2 and/or table 2 therein.

The present disclosure includes a crystalline polymorph of Relugolix, designated Form F. The crystalline Form F of Relugolix may be characterized by data selected from one or more of the following: an X-ray powder diffraction pattern substantially as depicted in FIG. 1 or in FIG. 7; an X-ray powder diffraction pattern having peaks at 6.9, 7.5, 9.5, 13.9 and 18.1 degrees 2-theta±0.2 degrees 2-theta; an FT-IR spectrum having peaks at 1720, 1680, 1626, 1595, 1528, 1460, 1412, 1313, 1237 and 1095 cm$^{-1}$±4 cm$^{-1}$; an FT-IR spectrum substantially as depicted in FIGS. 6a and/or 6b; and combinations of these data.

Crystalline Form F of Relugolix may be further characterized by data selected from one or more of the following: an X-ray powder diffraction pattern having peaks at 6.9, 7.5, 9.5, 13.9 and 18.1 degrees 2-theta±0.2 degrees 2-theta, and also having any one, two, three, four or five additional peaks selected from the group consisting of 10.2, 12.9, 19.1, 21.1 and 23.2 degrees 2-theta±0.2 degrees 2-theta; an FT-IR spectrum having peaks at 3477, 3298, 3223, 3069, 2991, 2952, 2862, 2827, 2782, 1720, 1680, 1626, 1595, 1528, 1460, 1412, 1384, 1350, 1313, 1237, 1212, 1180, 1149, 1113, 1095, 1032, 1014, 973, 936, 836, 808, 784, 769, 746, 727, 684, 647, 628 and 598 cm$^{-1}$ 4 cm$^{-1}$; and combinations of these data.

In embodiments, crystalline Form F of Relugolix may have a melting point of about 204° C. as measured by DSC, and/or of about 198° C. as measured by capillary method.

In embodiments, crystalline Form F of Relugolix is an iso-structural polymorph, i.e., it may be either anhydrous, a hydrate, preferably a hemi-hydrate, or a solvate.

Crystalline Form F of Relugolix may be characterized by each of the above characteristics alone or by all possible combinations, e.g., an XRPD pattern having peaks at 6.9, 7.5, 9.5, 13.9 and 18.1 degrees 2-theta±0.2 degrees 2-theta; an XRPD pattern as depicted in FIG. 1; an XRPD pattern as depicted in FIG. 1 and melting point of about 198° C. as measured by capillary method; and combinations thereof.

In one embodiment of the present disclosure, crystalline Form F of Relugolix is isolated.

Depending on any other crystalline polymorphs with which a comparison is made, crystalline Form F of Relugolix of the present disclosure has advantageous properties as described above. For example, crystalline Form F possesses advantageous solubility behavior at physiological pH values, such as 4.8 and/or 6.8, which are highly relevant for API absorption from oral dosage form.

The present disclosure further provides Form F substantially free of other solid state forms of Relugolix. In embodiments the Form F includes 20% or less, 15% or less, 10% or less, 5% or less, 2% or less or 1% or less of other solid state forms of Relugolix as determined by XPRD. In some embodiments the Form F includes 0.5% or less, 0.25% or less, 0.1% or less, or undetectable amounts of other solid state forms of Relugolix as determined by XRPD.

The present disclosure further includes a crystalline polymorph of Relugolix, designated Form G. The crystalline Form G of Relugolix may be characterized by data selected from one or more of the following: an X-ray powder diffraction pattern substantially as depicted in FIG. 2; an X-ray powder diffraction pattern having peaks at 5.4, 8.4, 10.7 and 12.1 degrees 2-theta±0.2 degrees 2-theta; and combinations of these data.

Crystalline Form G of Relugolix may be further characterized by an X-ray powder diffraction pattern having peaks at 5.4, 8.4, 10.7 and 12.1 degrees 2-theta±0.2 degrees 2-theta, and also having any one, two, three or four additional peaks selected from the group consisting of 6.9, 7.7, 17.4 and 19.2 degrees 2-theta±0.2 degrees 2-theta.

Crystalline Form G of Relugolix may be characterized by each of the above characteristics alone or by all possible combinations, e.g., an XRPD pattern having peaks at 5.4, 8.4, 10.7 and 12.1 degrees 2-theta±0.2 degrees 2-theta; an XRPD pattern as depicted in FIG. 2, and combinations thereof.

In one embodiment of the present disclosure, crystalline Form G of Relugolix is isolated.

In embodiments, the present disclosure relates to a polymorphically pure Form G of Relugolix; i.e., crystalline Relugolix Form G that is substantially free of any other forms, as described herein above. In embodiments, it is substantially free of crystalline Relugolix Form H. Accordingly, the content of crystalline Relugolix Form H in crystalline Relugolix Form G is measured by detecting and quantifying the described characteristic peaks of Form H. The characteristic peaks of crystalline Relugolix Form H used for the above described measurement can be selected from the peaks at about 8.4 and/or 19.2 degrees two theta±0.2 degrees two theta.

The above polymorphically pure Form G of Relugolix may be characterized by data selected from one or more of the following: an X-ray powder diffraction pattern substantially as depicted in FIG. 4; an X-ray powder diffraction pattern having peaks at 3.4, 5.6, 9.6, 13.3 and 17.4 degrees 2-theta±0.2 degrees 2-theta; and combinations of these data. Polymorphically pure Form G of Relugolix may be further characterized by an X-ray powder diffraction pattern having peaks at 3.4, 5.6, 9.6, 13.3 and 17.4 degrees 2-theta±0.2 degrees 2-theta, and also having any one, two, three, four or five additional peaks selected from 7.7, 11.7, 12.2, 23.5 and 25.7 degrees 2-theta±0.2 degrees 2-theta.

Polymorphically pure Form G of Relugolix may be characterized by each of the above characteristics alone/or by all possible combinations, e.g., an XRPD pattern having peaks at 3.4, 5.6, 9.6, 13.3 and 17.4 degrees 2-theta±0.2 degrees 2-theta; an XRPD pattern as depicted in FIG. 4, and combinations thereof.

The present disclosure further includes a crystalline polymorph of Relugolix, designated Form H. The crystalline Form H of Relugolix may be characterized by data selected from one or more of the following: an X-ray powder diffraction pattern substantially as depicted in FIG. 3; an X-ray powder diffraction pattern having peaks at 6.2, 8.6, 15.9, 19.0 and 19.6 degrees 2-theta±0.2 degrees 2-theta; and combinations of these data.

Crystalline Form H of Relugolix may be further characterized by an X-ray powder diffraction pattern having peaks at 6.2, 8.6, 15.9, 19.0 and 19.6 degrees 2-theta±0.2 degrees 2-theta, and also having any one, two, three or four additional peaks selected from 10.1, 11.5, 12.3 and 22.0 degrees 2-theta±0.2 degrees 2-theta.

Crystalline Form H of Relugolix may be characterized by each of the above characteristics alone or by all possible combinations, e.g., an XRPD pattern having peaks at 6.2, 8.6, 15.9, 19.0 and 19.6 degrees 2-theta±0.2 degrees 2-theta; an XRPD pattern as depicted in FIG. 3, and combinations thereof.

In one embodiment of the present disclosure, crystalline Form H of Relugolix is isolated.

The present disclosure further includes a crystalline polymorph of Relugolix, designated Form J. The crystalline Form J of Relugolix may be characterized as a having triclinic crystal system, having space group of P1 and having unit cell dimensions of about a=14.3 Å±0.5 Å, b=15.0 Å±0.5 Å, c=16.5 Å±0.5 Å and unit cell volume of about V=3082 Å$^3$±10 Å$^3$ when determined at 180 K.

Crystalline Form J of Relugolix may be further characterized by a calculated X-ray powder diffraction pattern as depicted in FIG. 8.

In one embodiment of the present disclosure, crystalline Form J of Relugolix is isolated.

Crystalline Form J of Relugolix may be a solvated, hydrated crystalline form. In embodiments crystalline Form J of Relugolix prepared according to Example 8 corresponds to hemi acetonitrile solvate, hemihydrate (the unit cell contains four molecules of Relugolix, two molecules of acetonitrile and two molecules of water).

Form J as described in any embodiment disclosed herein may be used to prepare Form F as described in any embodiment disclosed herein. In embodiments, the Form F is prepared from Form J by drying or partial drying (i.e., solvent removal or partial solvent removal), e.g., at a temperature of 30-80° C., for a sufficient time to prepare Form F as described in any embodiment herein (in embodiments 2-8 hours, in some embodiments 3-6, hours or about 4 to about 5 hours)

The present invention also describes amorphous Relugolix. The amorphous is typically characterized by an X-ray powder diffraction pattern substantially as depicted in FIG. 5.

The step of isolating Relugolix or a crystalline polymorph of Relugolix may be performed by crystallization.

The above crystalline polymorphs can be used to prepare other crystalline polymorphs of Relugolix, Relugolix salts and their solid state forms.

The present disclosure provides crystalline polymorphs of Relugolix for use in the preparation of pharmaceutical compositions including Relugolix and/or crystalline polymorphs thereof.

The present disclosure also encompasses the use of crystalline polymorphs of Relugolix of the present disclosure for the preparation of pharmaceutical compositions of crystalline polymorph Relugolix and/or crystalline polymorphs thereof.

The present disclosure includes processes for preparing the above mentioned pharmaceutical compositions. The processes include combining the crystalline polymorphs of Relugolix of the present disclosure with at least one pharmaceutically acceptable excipient.

Pharmaceutical formulations of the present invention contain any one or a combination of the solid state forms of Relugolix of the present disclosure, in embodiments crystalline Relugolix Form F. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, Relugolix and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any method well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, in embodiments a powdered or granulated solid composition of the disclosure, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Relugolix can be administered. Relugolix may be formulated for administration to a mammal, in embodiments a human, by injection. Relugolix can be formulated, for example, as a viscous liquid solution or suspension, in embodiments a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Relugolix and the pharmaceutical compositions and/or formulations of Relugolix of the present disclosure can be used as medicaments, in embodiments for the treatment of endometriosis, uterine leiomyoma, and/or prostate cancer.

The present disclosure also provides methods of treating endometriosis, uterine leiomyoma, and/or prostate cancer by administering a therapeutically effective amount of a crystalline polymorph of Relugolix of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

XRPD Method

Powder X-ray Diffraction was performed on an X-Ray powder diffractometer PanAlytical X'pert Pro; CuKα radiation λ=1.54187 (1.5419 Å); X'Celerator detector with active length 2.122 degrees 2-theta; laboratory temperature 25±3° C.; zero background sample holders. Prior to analysis, the samples were gently ground using a mortar and pestle to obtain a fine powder. The ground sample was adjusted into a cavity of the sample holder and the surface of the sample was smoothed using a cover glass.

Measurement Parameters:

| | |
|---|---|
| Scan range | 3-40 degrees 2-theta |
| Scan mode | continuous |
| Step size | 0.0167 degrees |
| Step size | 42 s |
| Sample spin | 60 rpm |
| Sample holder | zero background silicon plate |

FT-IR Method

KBr pellet was prepared and FTIR transmission spectrum was recorded on Nicolet 380 spectrometer, equipped with KBr beam splitter and DTGS KBr detector.

Instrument Parameters:

Spectral range: 4000-550 $cm^{-1}$
Resolution: 4.0 $cm^{-1}$
Number of scans: 64
Sample gain: 1
Optical velocity: 0.6329
Aperture: 100

Melting-Point Capillary Measurement

Melting point was measured by capillary method according to USP <741>: Equipment: Capillary automated melting point analyzer MPA100 OptiMelt;
Heating range: 35-205° C.;
Heating rate: 1.0° C./min;
Evaluation: An arithmetic mean of the clear point values in three parallel capillaries was adopted as a melting point result.

X-Ray Crystal Structure Determination

Data were collected on a Rigaku Xcalibur PX system equipped with Onyx CCD detector and a Cu Kα sealed tube (λ=1.5418 Å) with an Enhanced monochromator using combined φ and ω scans at 180 K. Data collection: CrysAlisPro CCD (Oxford Diffraction, 2002); cell refinement: CrysAlisPro RED; data reduction: CrysAlisPro RED; program used to solve structure: Sir92 (Altomare et al., 1994); and void calculation was done by Platon (Spek, 2003).

Oxford Diffraction (2002). CrysAlisPro. Version 171.31.7 Oxford Diffraction Ltd, 68 Milton Park, Abingdon, Oxfordshire OX14 4RX, England.

SIR92—Altomare, A., Cascarano, G., Giacovazzo, G., Guagliardi, A., Burla, M. C., Polidori, G., Camalli, M. (1994). J. Appl. Cryst. 27, 435.

PLATON ver. 191114—Spek, A. L. (2003). PLATON, A Multipurpose Crystallographic Tool, Utrecht University, Utrecht, The Netherlands.

DSC Measurement Parameters

Equipment: TA Discovery;
Crucibles: Aluminum Tzero pans with pin-holed Tzero hermetic lids, 40 μl;
Heating range: 25-300° C.;
Heating rate: 10° C./min;
Purging gas: Nitrogen;
Purging gas flow: 50 ml/min.

Preparation of Starting Materials

Relugolix can be prepared according to methods known from the literature (for example, see WO 2004/067535; WO 2014/051164; and J. Med. Chem., 2011, 54 (14), pp. 4998-5012).

Example 1. Preparation of Relugolix Form F

Relugolix (470 mg) was fully dissolved at Di-methylsulphoxide (DMSO, 2 ml) at room temperature and a solution was obtained. The solution was heated to a temperature of 35° C., and 18 ml of Ethyl-acetate were added; then, the solution was cooled down to 5° C. over a period of 30 minutes and was stirred for additional 30 minutes and a clear solution was obtained. At this stage, 50 ml of water was added to the clear solution. After the addition of water, the solution became cloudy and was stirred for 60 minutes, and placed in a refrigerator. After 5 days the crystals were collected by filtration, and dried on the filter for 30 minutes. The material was further dried at 50° C. for 5 hours under Nitrogen ($N_2$) stream.

Yield: 200 mg; dry material.

A sample was analyzed by XRPD; Form F was obtained. XRPD pattern is depicted in FIG. 1. The obtained product was hemihydrate form.

Example 2. Preparation of Relugolix Form G

Relugolix (50 mg) was suspended in dichloromethane (1 ml), the obtained suspension was heated up to temperature 38° C. during 120 minutes. A clear solution was obtained at around 22-23° C. The solution was then stirred at temperature 38° C. for 30 minutes; subsequently, the clear solution was cooled down during 120 minutes from 38° C. to the temperature (−5°) C and stirred at this temperature for 30 minutes. Filtration was performed and the obtained wet crystals were left for 30 minutes, on the filter under Nitrogen ($N_2$) stream.

Yield: around 20 mg of white wet solid.

A sample was analyzed by XRPD, Form G was obtained. XRPD pattern is depicted in FIG. 2.

Example 3. Preparation of Relugolix Form H

Relugolix (500 mg) was suspended in dichloromethane (10 ml). The obtained suspension was heated up to temperature 38° C. during 90 minutes. A clear solution was obtained at around 22-23° C. The solution was then stirred at temperature 38° C. for 30 minutes; subsequently, the clear solution was cooled down during 90 minutes from 38° C. to the temperature (−5°) C and stirred at this temperature for 30 minutes. Filtration was performed, and the obtained wet crystals were left for 30 minutes on the filter under Nitrogen ($N_2$) stream. The obtained material was dried on air for 16 hours at room temperature. Yield: 200 mg.

A sample was analyzed by XRPD, Form H was obtained. XRPD pattern is depicted in FIG. 3.

Example 4. Preparation of Relugolix Form G—Polymorphically Pure

Relugolix (3000 mg) was suspended in dichloromethane (60 ml). The obtained suspension was heated up to temperature of 32° C. over a period of 30 minutes. A clear solution was obtained at around 22-23° C. and was filtrated through a folded filter. The solution was then stirred at temperature of 20° C. for 5 minutes; subsequently, the clear solution was cooled down over a period of 60 minutes from 20° C. to the temperature (−5°) C and was stirred at this temperature for 3.5 hours. Then, filtration was performed, the mother liquor was reserved for the subsequent procedure and the obtained wet crystals were left for 30 minutes on the filter under Nitrogen ($N_2$) stream. A sample was analyzed by XRPD, polymorphically pure Form G was obtained. XRPD pattern is depicted in FIG. 4.

Example 5. Preparation of Amorphous Relugolix

The dichloromethane mother liquor isolated in Example 4 (50 ml) was evaporated into dryness using a rotary vacuum evaporator. The conditions of evaporation: temperature of the bath 40° C., vacuum 25 mbar. Time of evaporation 30 minutes.

Yield from evaporation: 2.2 grams of the amorphous substance.

A sample was analyzed by XRPD, amorphous was obtained. XRPD pattern is depicted in FIG. 5.

Example 6. Preparation of Relugolix Form F

Relugolix (50 mg, amorphous) was suspended in water and the obtained suspension was heated up to temperature of 95° C. over a period of about 2 hours. The suspension was then stirred at temperature of 95° C. for a period of about 30 minutes and then the suspension was cooled down to temperature of (−5°) C over a period of about 2 hours and was further stirred at temperature of (−5°) C for a period of about 30 minutes. The suspension was filtered and the obtained wet crystals were left for 15 minutes on the filter under Nitrogen ($N_2$) stream. Yield: 45 mg of white wet solid. A sample was analyzed by XRPD, Form F was obtained; the obtained product was hemihydrate.

Example 7. Preparation of Relugolix Form F (Hemihydrate)

Relugolix (5 grams) was suspended in acetonitrile (300 ml) and the obtained suspension was heated up to temperature of 78° C. over a period of about 30 minutes. A clear solution was obtained. Subsequently, the clear solution was cooled down over a period of about 1 hour from temperature of about 78° C. to temperature of about 20° C. and water (500 ml) was added over a period of about 60 minutes. The solution was stirred at this temperature for 30 minutes and then cooled down to temperature of about 2° C. over a period of about 60 minutes, and a cloudy solution was formed. The cloudy solution was then stirred at temperature of about 2° C. for 12 hours, then it was filtered and obtained wet crystals were left for 30 minutes on the filter under Nitrogen ($N_2$) stream. The crystals were then dried under stream of Nitrogen ($N_2$) at temperature of about 70° C. for 5 hours. A sample was analyzed by XRPD, Form F was obtained; the obtained product was a hemihydrate.

Example 8. Preparation of Relugolix Form F (Anhydrous)

The product obtained in Example 7 was further heated by a TGA apparatus to temperature of about 140° C. (heating rate 10° C./min). A sample was analyzed by XRPD, Form F was maintained; XRPD pattern is depicted in FIG. 7. The obtained product was anhydrous.

Example 9. Preparation of Relugolix Form J

Relugolix (100 mg) was dissolved in acetonitrile (8 ml). Water (6 ml) was added with stirring at ambient temperature, and the open vial was placed into a box at 4° C. overnight. Then, the volume of solution was reduced to about ⅔ on a vacuum evaporator and the reduced solution was placed again into a box at 4° C., overnight. Colorless crystals were formed and a sample was covered by paraffin oil after removal from mother's liquor. A sample was analyzed by Single X-ray crystallographic analysis (180K), Form J was obtained; the obtained product was a hemi acetonitrile solvate, hemihydrate. Calculated XRPD pattern is presented in FIG. 8.

Example 10. Preparation of Relugolix Form F

Relugolix (80 mg) was dissolved in THF (8.5 ml) and then water (8.5 ml) was added. The solution was put into a cooler at 4° C. for a period of about 12 hours. Then, the sample was divided into two equal parts. To the part A, additional volume of water (5 ml) was added. The volume of part B was reduced to about 2 on a vacuum evaporator. Both samples were placed again into the cooler at 4° C. for a period of about 12 hours, and crystals were formed. The mother liquor was poured out and removed and both samples were dried at 40° C. and 500 Pa for a period of 10 minutes. A sample was analyzed by XRPD, Form F was obtained, as a hemihydrate.

Example 11. Preparation of Relugolix Form F

Relugolix (80 mg) was dissolved in acetone (7.5 ml) and water (7.5 ml) was added. The solution was put into a cooler at 4° C. for a period of about 12 hours. Then, about ½ of solution was evaporated on vacuum evaporator and sample was placed again into the cooler at 4° C. for a period of about 12 hours and crystals were formed. The mother liquor was poured out and removed and sample was dried at 40° C. and 500 Pa for a period of 10 minutes. A sample was analyzed by XRPD, Form F was obtained.

The invention claimed is:
1. Crystalline Form F of Relugolix, characterized by data selected from one or more of the following:
   a) an X-ray powder diffraction pattern substantially as depicted in FIG. 1 or in FIG. 7;

b) an X-ray powder diffraction pattern having peaks at 6.9, 7.5, 9.5, 13.9 and 18.1 degrees 2-theta±0.2 degrees 2-theta;
c) an FT-IR spectrum having peaks at 1720, 1680, 1626, 1595, 1528, 1460, 1412, 1313, 1237 and 1095 cm$^{-1}$±4 cm$^{-1}$;
d) an FT-IR spectrum as depicted in FIG. 6a and/or 6b; and
e) combinations of these data.

2. The crystalline Form F of Relugolix according to claim 1, characterized by an X-ray powder diffraction pattern having peaks at 6.9, 7.5, 9.5, 13.9 and 18.1 degrees 2-theta±0.2 degrees 2-theta, and also having any one, two, three, four or five additional peaks selected from the group consisting of 10.2, 12.9, 19.1, 21.1 and 23.2 degrees 2-theta±0.2 degrees 2-theta.

3. The crystalline Form F of Relugolix according to claim 1, characterized by an FT-IR spectrum having peaks at 3477, 3298, 3223, 3069, 2991, 2952, 2862, 2827, 2782, 1720, 1680, 1626, 1595, 1528, 1460, 1412, 1384, 1350, 1313, 1237, 1212, 1180, 1149, 1113, 1095, 1032, 1014, 973, 936, 836, 808, 784, 769, 746, 727, 684, 647, 628 and 598 cm$^{-1}$±4 cm$^{-1}$.

4. The crystalline Form F of Relugolix according to claim 1, characterized by a melting point of about 204° C. as measured by DSC.

5. The crystalline Form F of Relugolix according to claim 1, characterized by a melting point of about 198° C. as measured by capillary method.

6. The crystalline Form F of Relugolix according to claim 1, wherein the crystalline form is an anhydrous form.

7. The crystalline Form F of Relugolix according to claim 1, wherein the crystalline form is a hydrate form.

8. The crystalline Form F of Relugolix according to claim 1, which contains not more than 5% (w/w) of any other crystalline form of Relugolix.

9. The crystalline Form F of Relugolix according to claim 1, which contains not more than 1% (w/w) of any other crystalline form of Relugolix.

10. A pharmaceutical composition comprising crystalline Form F of Relugolix according to claim 1.

11. A pharmaceutical formulation comprising crystalline Form F of Relugolix according to claim 1, and at least one pharmaceutically acceptable excipient.

12. A process for preparing the pharmaceutical formulation according to claim 11, comprising combining the crystalline Form F of Relugolix, with at least one pharmaceutically acceptable excipient.

* * * * *